United States Patent
Huldin et al.

(10) Patent No.: US 10,537,393 B2
(45) Date of Patent: Jan. 21, 2020

(54) MEDICAL DEVICE FOR SURGICAL NAVIGATION SYSTEM AND CORRESPONDING METHOD OF MANUFACTURING

(71) Applicant: IZI MEDICAL PRODUCTS, LLC, Owings Mills, MD (US)

(72) Inventors: Nelson L. Huldin, Alexandria, VA (US); Greg Groenke, Owings Mills, MD (US); Holger-Claus Rossner, Feldkirchen B. Muenchen (DE)

(73) Assignee: IZI Medical Products, LLC, Owings Mills, MD (US)

( * ) Notice: Subject to any disclaimer, the term of this patent is extended or adjusted under 35 U.S.C. 154(b) by 1051 days.

(21) Appl. No.: 14/245,141

(22) Filed: Apr. 4, 2014

(65) Prior Publication Data

US 2015/0282736 A1   Oct. 8, 2015

(51) Int. Cl.
*A61B 5/06* (2006.01)
*A61B 34/20* (2016.01)
(Continued)

(52) U.S. Cl.
CPC .............. *A61B 34/20* (2016.02); *A61B 5/064* (2013.01); *A61B 5/066* (2013.01); *A61B 34/00* (2016.02); *A61B 90/39* (2016.02); *A61B 2034/2068* (2016.02); *A61B 2090/3983* (2016.02); *A61B 2505/05* (2013.01); *A61B 2560/00* (2013.01);
(Continued)

(58) Field of Classification Search
CPC ......... A61B 17/00; A61B 5/064; A61B 5/066; A61B 90/39; A61B 2034/2068; A61B 2090/3983; A61B 2505/05; A61B 2560/0406; A61B 2562/12; Y10T 29/49826
See application file for complete search history.

(56) References Cited

U.S. PATENT DOCUMENTS 5,232,452 A   8/1993   Russell et al.
5,368,030 A   11/1994  Zinreich et al.
(Continued)

FOREIGN PATENT DOCUMENTS

EP   1498688 A1   1/2005
JP   8-52115      2/1996
(Continued)

OTHER PUBLICATIONS

International Search Report and Written Opinion dated Dec. 24, 2014 in corresponding International Application No. PCT/IB2014/060490.
(Continued)

*Primary Examiner* — Amanda Lauritzen Moher
(74) *Attorney, Agent, or Firm* — Miles & Stockbridge P.C.; Ajay Jagtiani

(57) ABSTRACT

A device and manufacturing method for a surgical navigation system, comprising a frame member having an attachment location and a rigid mounting device disposed in the attachment location. The frame member comprises an upper straight portion connected to a lower straight portion via a bent portion, wherein the lower straight portion comprises a plurality of mounts each having a top surface. A centerline extending through the rigid mounting device is level with each of the top surfaces.

30 Claims, 4 Drawing Sheets

(51) Int. Cl.
  *A61B 34/00* (2016.01)
  *A61B 90/00* (2016.01)
(52) U.S. Cl.
  CPC ... *A61B 2560/0406* (2013.01); *A61B 2562/12* (2013.01); *Y10T 29/49826* (2015.01)

(56) References Cited

U.S. PATENT DOCUMENTS

| | | | |
|---|---|---|---|
| 5,383,233 A | 1/1995 | Russell | |
| 5,427,099 A | 6/1995 | Adams | |
| 5,517,990 A | 5/1996 | Kalfas et al. | |
| 5,732,703 A * | 3/1998 | Kalfas | A61B 17/3403 |
| | | | 600/407 |
| 5,735,795 A | 4/1998 | Young et al. | |
| 5,743,899 A | 4/1998 | Zinreich | |
| 5,776,064 A | 7/1998 | Kalfas et al. | |
| 5,980,535 A | 11/1999 | Barnett et al. | |
| 6,041,094 A | 3/2000 | Russell | |
| RE36,641 E | 4/2000 | Griffin | |
| 6,167,145 A | 12/2000 | Foley et al. | |
| 6,333,971 B2 | 12/2001 | McCrory et al. | |
| 6,419,680 B1 | 7/2002 | Cosman et al. | |
| 6,491,699 B1 * | 12/2002 | Henderson | A61B 19/52 |
| | | | 600/414 |
| 6,687,533 B1 | 2/2004 | Hirano et al. | |
| 6,714,628 B2 | 3/2004 | Broyles et al. | |
| 6,862,470 B2 | 3/2005 | Burbank et al. | |
| 6,928,146 B2 | 8/2005 | Broyles et al. | |
| 6,985,558 B1 | 1/2006 | Russell | |
| 7,263,159 B2 | 8/2007 | Russell | |
| 7,313,430 B2 | 12/2007 | Urquhart et al. | |
| 7,702,378 B2 | 4/2010 | Bolan et al. | |
| 8,032,204 B2 | 10/2011 | Solar et al. | |
| 8,467,851 B2 | 6/2013 | Mire et al. | |
| 2001/0004395 A1 | 6/2001 | McCrory et al. | |
| 2003/0069591 A1 * | 4/2003 | Carson | A61B 17/154 |
| | | | 606/130 |
| 2004/0097952 A1 * | 5/2004 | Sarin | A61B 5/103 |
| | | | 606/102 |
| 2004/0116802 A1 | 6/2004 | Jessop et al. | |
| 2004/0267242 A1 | 12/2004 | Grimm et al. | |
| 2005/0187562 A1 * | 8/2005 | Grimm | A61F 2/4603 |
| | | | 606/130 |
| 2007/0016009 A1 * | 1/2007 | Lakin | A61B 19/5244 |
| | | | 600/424 |
| 2007/0233121 A1 * | 10/2007 | Carson | A61B 17/154 |
| | | | 378/205 |
| 2008/0200794 A1 | 8/2008 | Teichman et al. | |
| 2010/0016859 A1 | 1/2010 | Plassky et al. | |
| 2010/0100081 A1 * | 4/2010 | Tuma | A61B 34/20 |
| | | | 606/1 |
| 2010/0113912 A1 | 5/2010 | Traboulsi et al. | |
| 2011/0263971 A1 * | 10/2011 | Nikou | A61B 19/5244 |
| | | | 600/424 |

FOREIGN PATENT DOCUMENTS

| | | |
|---|---|---|
| JP | H852115 A | 2/1996 |
| JP | H0852115 A | 2/1996 |
| JP | 2002-510214 | 4/2002 |
| JP | 2002510214 A | 4/2002 |
| WO | 96/11624 A2 | 4/1996 |
| WO | 9611624 A2 | 4/1996 |
| WO | 2012/152879 A1 | 11/2012 |
| WO | 2012152879 A1 | 11/2012 |

OTHER PUBLICATIONS

Japanese Office Action dated Feb. 28, 2017 in corresponding Japanese Patent Application No. 2016-560677.
Office Action dated Nov. 28, 2016 issued in corresponding Canadian Patent Application No. 2,943,605.
Final Official Action received in Japanese Application No. 2016-560677 dated Aug. 29, 2017.
English translation of Final Official Action received in Japanese Application No. 2016-560677 dated Aug. 29, 2017.
JP Office Action dated Nov. 27, 2018 in corresponding Japanese Patent Application No. 2017-251452.
Extended European Search Report received in European Application No. 14888207.9 dated Oct. 20, 2017.
Extended European Search Report received in European Application No. 17162328.3 dated Oct. 20, 2017.

* cited by examiner

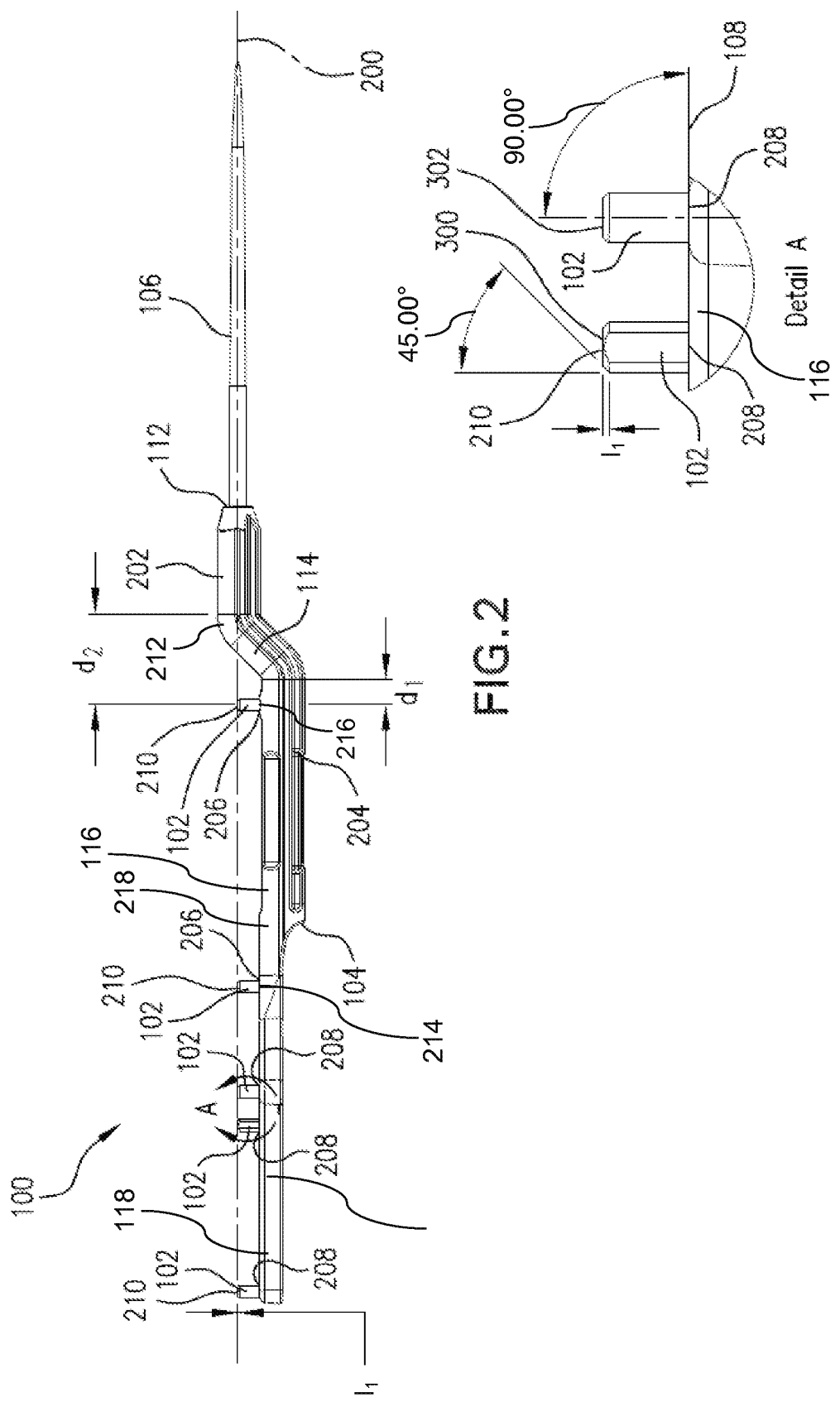

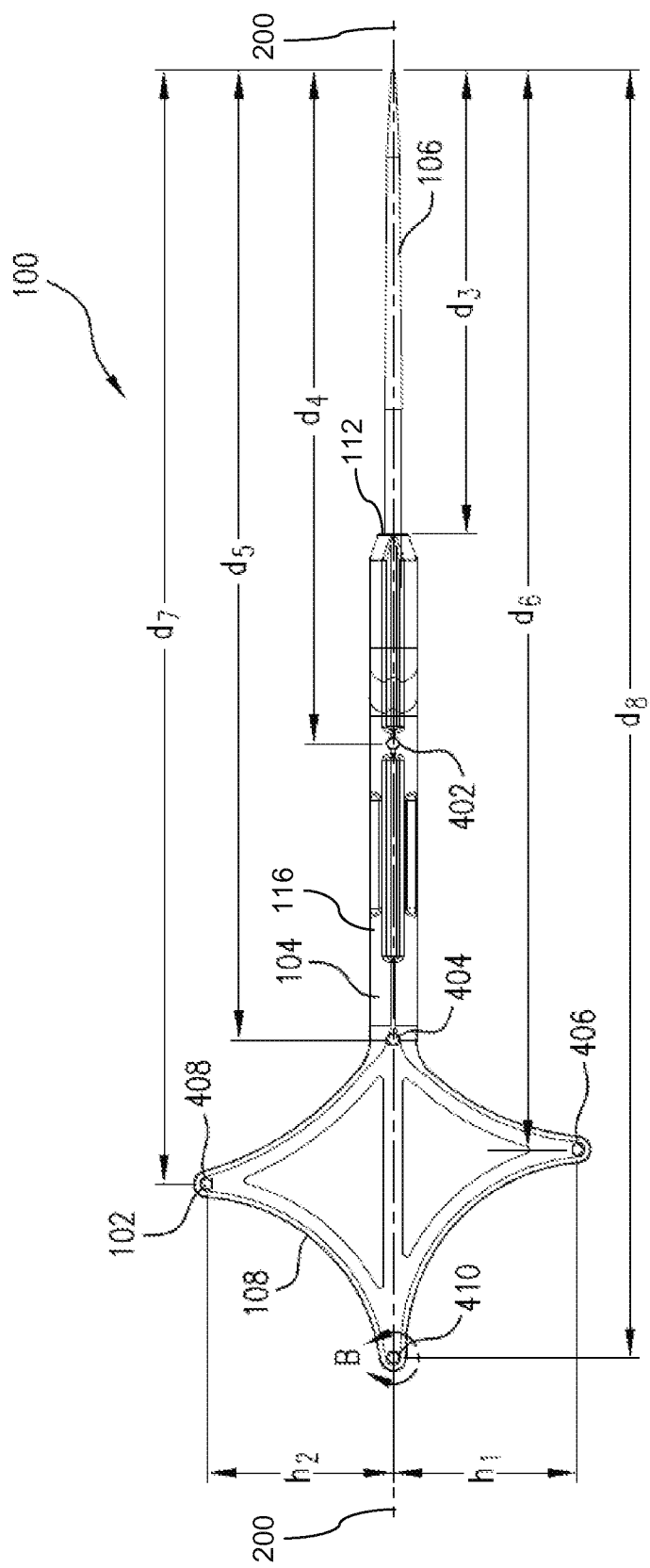
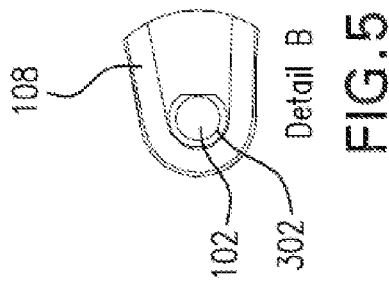
FIG. 4
FIG. 5

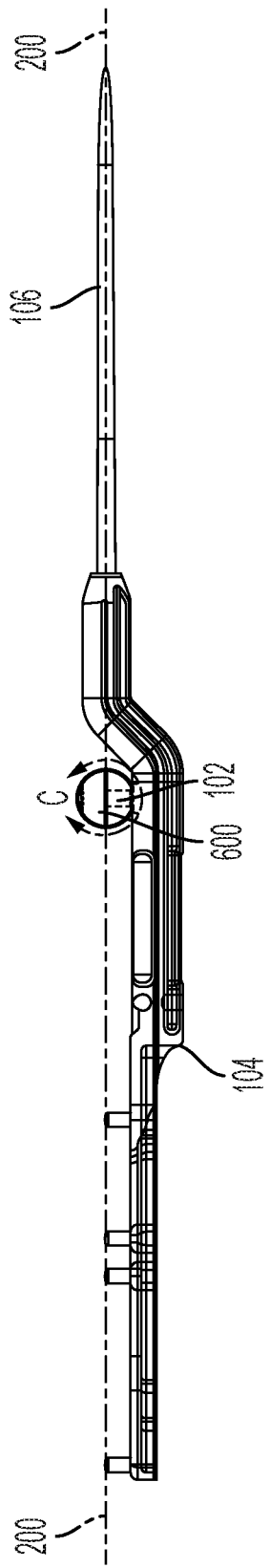
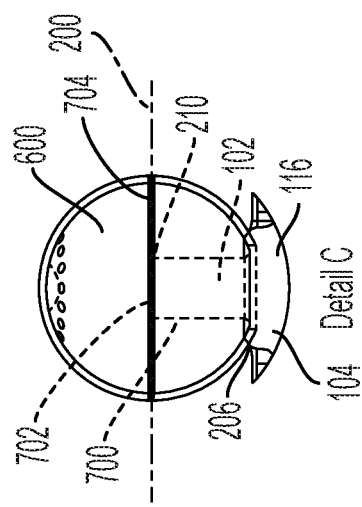
FIG. 6
FIG. 7

MEDICAL DEVICE FOR SURGICAL NAVIGATION SYSTEM AND CORRESPONDING METHOD OF MANUFACTURING

BACKGROUND

Field of the Invention

The present invention relates generally to surgical navigation systems. More particularly, the present invention relates to a medical device for use in a surgical navigation system.

Related Art

Surgical navigation systems are employed in a variety of surgical applications, for example, in neurosurgery, oral, maxillofacial and facial surgery, ear nose and throat (ENT) surgery or also for limb implantation in orthopedic surgery. Based on three-dimensional patient image data, which are obtained by means of X-ray images, computer tomography (CT), magnetic resonance tomography (MRT) and/or positron emission tomography (PET), surgical navigation systems of this type enable the position of medical instruments to be visualized in real-time in the patient image data in order to thereby assist the surgeon during operable procedures.

To this end, it may be necessary to record and monitor the position and orientation of the patient or a specific body part on which a surgical procedure is to be carried out—also referred to as "tracking." Conventional referencing devices, employed within such surgical navigation systems, for example, have been used usually comprising reference frames to which marking elements such as light-reflecting, spherical marker elements are attached. The light-reflecting spherical marker elements allow a stereo camera system of the navigation system to record the precise position and orientation of the referencing device.

Prior art reference frames are traditionally reusable units that may be subjected to a sterilization process after use. The marker elements of the reference frame may also be removed and replaced. As is often the case, for example, the reference frame contains mounting assembly structures to which the marker elements are mounted. However there are concerns in quality control processes to ensure total elimination of infectious diseases, such as mad cow disease, for example, during the aforementioned sterilization process of the reference frame and/or the marker elements. In addition, there exists a risk in breakage of the mounting assembly structures of the reference frame. Furthermore, such mounting assembly structures may become bent or skewed during removal or attachment of the marker elements. This introduces misalignment of the marker elements and, hence, possibly the reference frame itself for use in the surgical navigation system. Additionally, errors and inaccuracies in location, for example, are introduced giving rise to critical errors that may be introduced during a misaligned setup.

It is, therefore, an object of the present invention to overcome the deficiencies of the prior art to provide an improved reference frame capable of eliminating or greatly reducing errors/inaccuracies in misalignment during setup. It is a further goal of the present invention to provide a method and apparatus that achieves the elimination or reduction of the transfer of infectious diseases and other possible contaminants within the surgical navigation system. It is desirable to achieve a method and apparatus that maintains a dependable fixed position of marker elements mounted on the referencing frame during operational procedures that eliminates the need to recalibrate the system. Such reference frame should be easily and accurately reproducible.

SUMMARY

The foregoing needs are met, to a great extent, by the present invention, wherein in one aspect a device is provided that in some embodiments comprises a frame member having an attachment location and a rigid mounting device disposed in the attachment location. The frame member comprises an upper straight portion connected to a lower straight portion via a bent portion, wherein the lower straight portion comprises a plurality of mounts each having a top surface. A centerline extending through the rigid mounting device is level with each of the top surfaces.

In accordance with another embodiment of the present invention, a method is provided that in some embodiments comprises bending a frame member to form an upper straight portion and a lower straight portion connected by a bent portion and mounting a rigid mounting device to an attachment location of the upper straight portion. The method may also include connecting a plurality of mounts on the lower straight portion, wherein each plurality of mounts has a top surface. The bent portion is configured to align with a centerline extending through the center length of the mounting device to be level with all of the top surfaces. Additionally, the method may also include mounting marker elements on each mount and aligning a centerline of each marker element with the top surface to form a pre-attached marker assembly ready for use.

In accordance with yet another embodiment of the present invention, a method is provided that in some embodiments comprises bending a frame member to form an upper straight portion and a lower straight portion connected by a bent portion and mounting a rigid mounting device to an attachment location of the upper straight portion. The method may also comprise mounting marker elements on the frame member, wherein the bent portion is configured to align a centerline extending through the center length of the mounting device level with a centerline of each marker element to form a pre-attached marker assembly ready for use.

There has thus been outlined, rather broadly, certain embodiments of the invention in order that the detailed description of the invention herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as in the abstract, are for the purpose of description and should not be regarded as limiting.

As such, those skilled in the art will appreciate that the concept upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Still other aspects, features and advantages of the present invention are readily apparent from the following detailed description, simply by illustrating a number of exemplary embodiments and implementations, including the best mode contemplated for carrying out the present invention. The present invention also is capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The accompanying drawings, which are incorporated herein and constitute to part of this specification, illustrate exemplary embodiments of the invention, and, together with the general description given above and the detailed description given below, serve to explain the features of the invention.

FIG. 2 is a side view of the disposable medical device of FIG. 1 for a surgical navigation system according to an embodiment of the present invention.

FIG. 3 is a detail view a section of the disposable medical device of FIG. 2 according to one embodiment of the present invention.

FIG. 4 is a top view of the disposable medical device of FIG. 1 for a surgical navigation system according to an embodiment of the present invention.

FIG. 5 is a detail view a section of the disposable medical device of FIG. 4 according to one embodiment of the present invention.

FIG. 6 is a side view of the disposable medical device of FIG. 1 including a mounted marker element according to an embodiment of the present invention.

FIG. 7 is a detail view of the mounted marker element of FIG. 6 according to one embodiment of the present invention.

DETAILED DESCRIPTION OF THE PREFERRED EMBODIMENTS

Definitions

Figure 1:
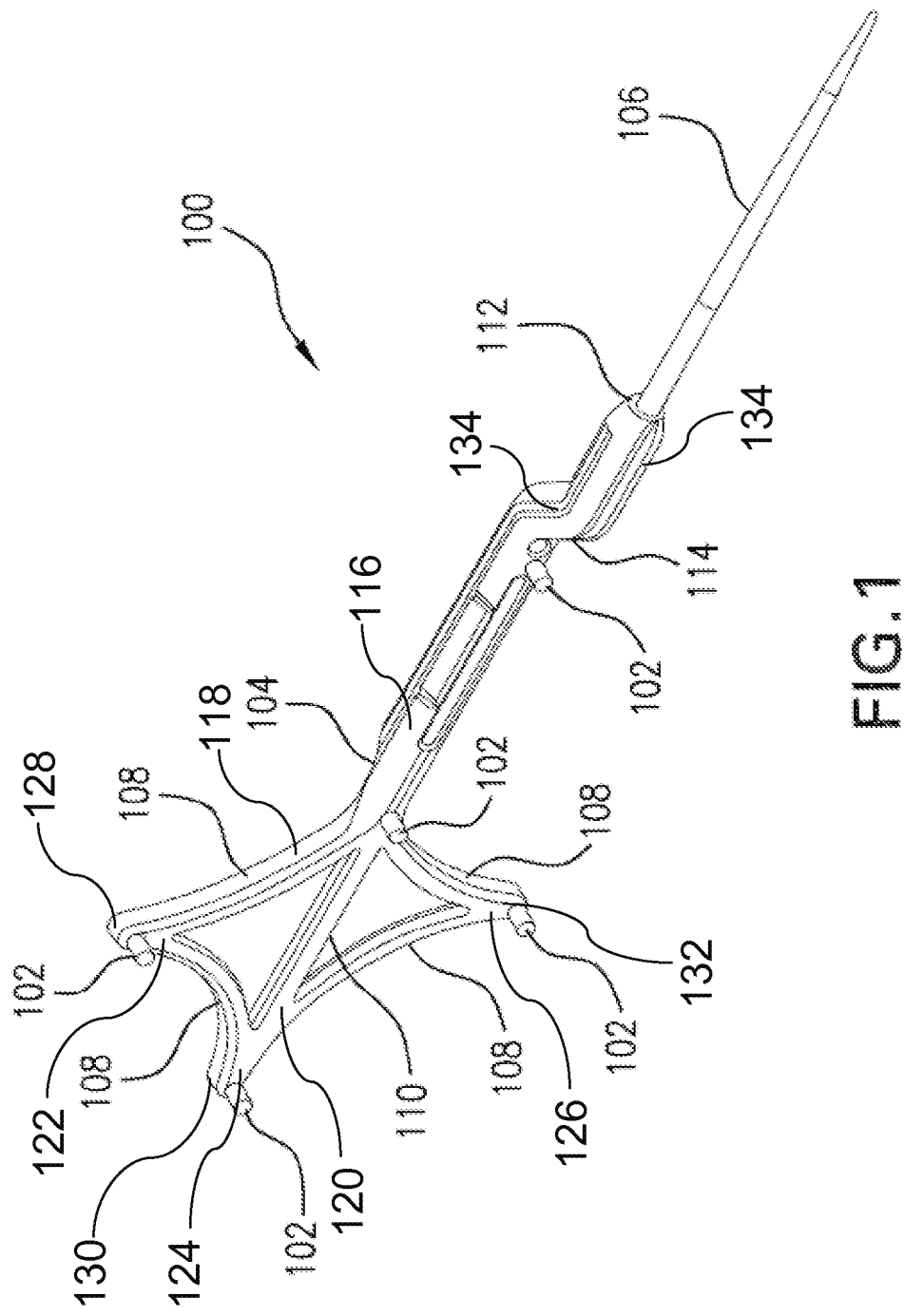
FIG. 1 is a perspective view of a disposable medical device for a surgical navigation system according to an embodiment of the present invention.

Where the definition of terms departs from the commonly used meaning of the term, applicant intends to utilize the definitions provided below, unless specifically indicated.

For the purposes of the present invention, directional terms such as "top", "bottom", "upper", "lower", "above", "below", "left", "right", "horizontal", "vertical", "upward", "downward", etc., are merely used for convenience in describing the various embodiments of the present invention.

For purposes of the present invention, the term "astroid" refers to a geometric design of a hypocycloid with four cusps, the curve of which includes a variety of names, including tetracuspid, cubocycloid, and paracycle.

For purposes of the present invention, the term "indicia" refers distinctive marks, characteristic markers or indications.

For purposes of the present invention, the term "registering" refers to a process for determining the geometric relationship between an anatomic structure(s) of interest and a dimensional (3D) computer image constructed, for example, from the preoperative CT scan. By way of this registration, a correct, spatial reference between the 3D image data and the position and orientation of the body part of the patient, observed by means of referencing device, can be produced.

For purposes of the present invention, the term "surgical navigation" refers to computer assisted surgery (CAS) representing a surgical concept and set of methods that use computer technology for pre-surgical planning and for guiding or performing surgical interventions. CAS is also known as computer aided surgery, computer assisted intervention, image guided surgery and surgical navigation.

For purposes of the present invention, the term "surgical navigation system" refers a system that allows visualization of an operative site and surgical instruments simultaneously and relates them to the patient's diagnostic images (e.g., computed tomographic (CT) scans and magnetic resonance imaging (MRI)). A surgical navigation system is used to guide the surgeon's movements during an operation. It may display the real-time position of each instrument and anatomical structure. These systems are used in orthopedics, ENT, neurology and other surgical specialties. Real-time observations occur via. MRI, scanner, video camera or another imaging process. Navigation data are incorporated into the image to help the surgeon determine precise position within the organism. Medical imaging is sometimes used to plan an operation before surgery. Data integration enables the system to compare the actual position of the target object with the ideal location established during the planning phase. Such systems may be mechanical, electromagnetic or optical. The most common are optical devices, either passive or active. In the former, cameras locate specific markers such as reflective targets, particular shapes or colors. Active systems locate LEDs.

For purposes of the present invention, the term "x-direction" refers to the direction aligned with the x-axis of a coordinate system.

For purposes of the present invention, the term "y-direction" refers to the direction aligned with the y-axis of a coordinate system.

For purposes of the present invention, the term "z-direction" refers to the direction aligned with the z-axis of a coordinate system.

Description

The invention will now be described with reference to the drawing figures, in which like reference numerals refer to like parts throughout. The following detailed description is of example embodiments of the presently claimed invention with references to the accompanying drawings. Such description is intended to be illustrative and not limiting with respect to the scope of the present invention. Such embodiments are described in sufficient detail to enable one of ordinary skill in the art to practice the subject invention, and it will be understood that other embodiments may be practiced with some variations without departing from the spirit or scope of the subject invention.

The disclosed invention contemplates the fabrication and use of a disposable, single-use medical device. Turning to FIG. 1, a disposable medical device 100 for use in a surgical navigation system is illustrated including a reference frame of the disclosed invention. The reference frame comprises a trackable target probe 104 coupled to a mounting device 106 at a mounting or attachment location 112. Attachment location 112 may comprise a receiving structure such as a hole for accepting and securing an end of mounting device 106.

Trackable target probe 104 comprises a frame member 116. In one disclosed embodiment, frame member 116 includes a bend or gooseneck bend 114 which extends into a flared extension portion 118. A plurality of ridges 134 may be designed into the framework of frame member 116 to provide increased structural integrity to medical device 100.

The embodiment of the disclosed flared extension portion 118 includes an asymmetric configuration. The asymmetric configuration may include an astroid design 120, for example, having four cusps 108. While four exemplary cusps 108 are shown for illustrative purposes, one skilled in the art will readily appreciate more or fewer cusps 108 may be employed by disclosed embodiments. A support member 110 extends between cusps 108 to provide strength to the integral design. The asymmetric astroid design 120 of flared extension portion 118 provides three notable extensions: first extension 122, second extension 124 and third extension 126. Mounting posts 102 are disposed on flared extension portion 118. In some embodiments, mounting posts 102 are generally disposed at end points 128, 130, and 132 of first extension 122, second extension 124 and third extension 126, respectively. Mounting posts 102 may also be selectively mounted at other locations of trackable target probe 104, as described below.

Turning to FIG. 2, an embodiment of frame member 116 depicts gooseneck bend 114 to include a first straight portion 202, transitioning and extending into a bent portion 212, transitioning and extending into a second straight portion 204 before frame member 116 finally extends into flared extension portion 118. As viewed from the illustrated side view, first straight portion 202 may be regarded as an upper straight portion, and second straight portion 204 may be regarded as lower straight portion.

As stated above, mounting posts 102 are disposed on flared extension portion 118 at prescribed locations 208. Additional mounting posts 102 may be selectively attached, for example, on lower straight portion 204. In a preferred embodiment, one mounting post 102 is disposed on lower straight portion 204 generally at a location 214, approximately right before a transition of an extended portion 218 of the lower straight portion 204 into the flared extension portion 118. Another mounting post 102 is preferably disposed on lower straight portion 204, generally at a location 216 approximately slightly before a transition into bent portion 212. Location 216 may be determined, for example, by measuring a distance $d_1$ from a center line extending upwardly through the elongated portion of mounting post 102 to a point located on lower straight portion 204 right at bend 114. Hence, $d_1$ may measure 0.24 inches±0.01. Location 216 may also be determined, for example, by measuring a distance $d_2$ from a center line extending upwardly through the elongated portion of mounting post 102 to a point located on upper straight portion 206 right at bend 114. Hence, $d_2$ may measure 0.88 inches±0.01. Thus, a prescribed number of mounting posts 102 are disposed at prescribed locations 206 along extended portion 218 of the lower straight portion 204.

Attachment location 112 is designed and configured to accept and maintain mounting device 106 such that a centerline 200 runs generally through the center length of mounting device 106, through the center of upper straight portion 202 and extends down and along the middle of the rest of frame member 116 see top view of FIG. 4). As depicted in the side view of FIG. 2, centerline 200 also aligns with the top 210 of each mounting post 102 such that centerline 200 extending through is level with each of top surfaces 210. Thus, a horizontal plane running through centerline 200 aligns each top 210 of mounting post 102 with the center of upper straight portion 202, mounting device 106 and with each other.

To this extent, and to achieve and maintain the alignment of centerline 200, frame member 116 and mounting device 106 are manufactured to a sufficient rigidity. In some disclosed embodiments, frame member 116 and mounting device 106 may be manufactured from plastic materials. For example, the manufacturing process may comprise molded plastic materials which allows reproducibility and accuracy in design.

In some preferred embodiments, the plastic comprises polycarbonate, polyetherimide (PEI) or another glass filled polymer such as poiyetheretherketone (PEEK). A PEEK product description includes a high performance thermoplastic, unreinforced polyetheretherketone, semi crystalline, including granules for injection molding and extrusion, standard flow, FDA food contact compliant, color natural/ beige. PEEK is applicable for applications for higher strength and stiffness as well as high ductility. It is chemically resistant to aggressive environments and suitable for sterilization for medical and food contact applications. PEEK property data table is provided as follows:

TABLE 1

|  | Nominal Value (English) | Nominal Value (SI) | Test Method |
|---|---|---|---|
| Physical |  |  |  |
| Density |  |  | ISO 1183 |
| Crystalline | 1.30 g/cm$^3$ | 1.30 g/cm$^3$ |  |
| Amorphous | 1.26 g/cm$^3$ | 1.26 g/cm$^3$ |  |
| Mechanical |  |  |  |
| Tensile Modulus (73° F. (23° C.)) | 537000 psi | 3700 Mpa | ISO 527-2 |
| Tensile Stress (Yield, 73° F. (23° C.)) | 14500 psi | 100 Mpa | ISO 527-2 |
| Tensile Strain (Break, 73° F. (23° C.)) | 45% | 45% | ISO 527-2 |
| Flexural Strength |  |  |  |
| 73° F. (23° C.) (at yield) | 23900 psi | 165 Mpa |  |
| 3.5% Strain, 73° F. (23° C.) | 18100 psi | 125 Mpa |  |
| 257° F. (125° C.) | 12300 psi | 85.0 Mpa |  |
| 347° F. (175° C.) | 2610 psi | 18.0 Mpa |  |
| 527° F. (275° C.) | 1890 psi | 13.0 MPa |  |

TABLE 1-continued

| | Nominal Value (English) | Nominal Value (SI) | Test Method |
|---|---|---|---|
| Compressive Stress | | | ISO 604 |
| 73° F. (23° C.) | 18100 psi | 125 Mpa | |
| 248° F. (120° C.) | 10200 psi | 70.0 Mpa | |
| Hardness | | | |
| Shore Hardness (Shore D, 73° F. (23° C.)) | 85 | 85 | ISO 868 |
| Thermal | | | |
| Heat Deflection Temperature | | | ISO 75-2/A |
| 264 psi (1.8 MPa), Un-annealed | 306° F. | 152° C. | |
| Glass Transition Temperature | 289° F. | 143° C. | ISO 11357-2 |
| Melting Temperature | 649° F. | 343° C. | ISO 11357-3 |
| CLTE | | | |
| Flow: <289° F. (<143° C.) | 0.000025 in/in/° F. | 0.000045 cm/cm/° C. | |
| Flow: >289° F. (>143° C.) | 0.000067 in/in/° F. | 0.00012 cm/cm/° C. | |
| Transverse: | | | |
| <289° F. (< 143° C.) | 0.000031 in/in/° F. | 0.000055 cm/cm/° C. | |
| >289° F. (>143° C.) | 0.000078 in/in/° F. | 0.00014 cm/cm/° C. | |
| Specific Heat (73° F. (23° C.)) | 0.526 Btu/lb/° F. | 2200 J/kg/° C. | DSC |
| Thermal Conductivity (73° F. (23° C.)) | 2.0 Bti-in/hr/ft$^2$/° F. | 0.29 W/m/K | ISO 22007-4 |
| Electrical | | | IEC 60093 |
| Volume Resistivity | | | |
| 73° F. (23° C.) | 1.0E+16 ohm · cm | 1.0E+16 ohm · cm | |
| 257° F. (125° C.) | 1.0E+35 ohm · cm | 1.0E+15 ohm · cm | |
| 437° F. (225° C.) | 1.0E+9 ohm· cm | 1.0E+9 ohm · cm | |
| Electric Strength | | | IEC 60093 |
| 0.00197 in (0.0500 mm) | 4800 V/mil | 190 kV/mm | |
| 0.0787 in (2.00 mm) | 580 V/mil | 23 kV/mm | |
| Dielectric Constant | | | |
| 73° F. (23° C.), 50 Hz | 3.00 | 3.00 | |
| 73° F. (2.3° C.), 1 kHz | 3.10 | 3.10 | |
| 257° F. (125° C.), 50 Hz | 4.50 | 4.50 | |
| Fill Analysis | | | ISO 11443 |
| Melt Viscosity (752° F. (400° C.)) | 350 Pa · s | 350 Pa · s | |
| Injection | | | |
| Drying Temperature | 248 to 302° F. | 120 to 150° C. | |
| Drying Time | 3.0 to 5.0 hr | 3.0 to 5.0 hr | |

A polycarbonate product description includes a glass and carbon fiber reinforced, mineral and process additive filled structural compound material. The polycarbonate product may be offered in all infinity base resins. The polycarbonate product provides improvements in strength, stiffness, creep resistance, fatigue endurance and impact and dimensional stability. Additional properties include increased thermal heat deflection temperature or heat distortion temperature (HDTUL) and long term heat resistance. Polycarbonate property data table is provided as follows:

TABLE 2

| | Nominal Value (English) | Nominal Value (SI) | Test Method |
|---|---|---|---|
| Physical | | | |
| Specific Gravity | 1.34 | 1.34 g/cm$^3$ | ASTM D792 |
| Specific Volume | 20.7 in$^3$/lb | 0.747 cm$^3$/g | |
| | | 1.26 g/cm$^3$ | |
| Mechanical | | | |
| Tensile Strength (Yield) | 16000 psi | 110 MPa | ASTM D638 |
| Tensile Elongation (Yield) | 2.0 to 4.0% | 2.0 to 4.0%i | ASTM D638 |
| Flexural Modulus | 1.00E+6 psi | 6890 MPa | ASTM D790 |
| Flexural Strength | 25000 psi | 172 Mpa | ASTM D790 |
| Thermal | | | |
| Deflection Temperature Under Load | | | ASTM D648 |
| 264 psi (1.8 MPa), Unannealed | 295° F. | 146° C. | |
| CLTE - Flow | 0.000015 in/in °/F. | 0.000027 cm/cm °/C. | ASTM D696 |
| Electrical | | | |
| Surface Resistivity | 1.0E+7 ohm | 1.0E+17 ohm | ASTM D257 |

TABLE 2-continued

|  | Nominal Value (English) | Nominal Value (SI) | Test Method |
|---|---|---|---|
| Injection | | | |
| Drying Temperature | 250° F. | 121° C. | |
| Drying Time | 4.0 hr | 4.0 hr | |
| Processing (Melt) Temp. | 540 to 630° F. | 282 to 332° C. | |
| Mold Temperature | 200° F. | 93.3° C. | |

Polyetherimide (PEI) property data table is provided as follows:

TABLE 3

|  | English | SI Metric | ASTM TEST |
|---|---|---|---|
| Performance | | | |
| Specific Gravity | 1.27 | 1.27 | D 792 |
| Melt Flow Rate | | | |
| #337° C./6.6 kg | 17.80 g/10 min | 17.80 g/10 min | D 1238 |
| Molding Shrinkage | | | |
| ⅛ in (3.2 mm) section | 0.0050-0.0070 in/in | 0.50-0.70% | D 955 |
| Mechanical | | | |
| Tensile Strength | 16000 psi | 110 MPa | D 638 |
| Tensile Elongation | >10.0% | >10.0% | D 638 |
| Tensile Modulus | $0.52 \times 10^6$ psi | 3585 MPa | D 638 |
| Flexural Strength | 24000 psi | 165 MPa | D 790 |
| Flexural Modulus | $0.50 \times 10^6$ psi | 3448 MPa | D 790 |
| General Processing for Injection Molding | | | |
| Injection Pressure | 12000-18000 psi | 83-124 MPa | |
| Melt Temperature | 670-750° F. | 354-399° C. | |
| Mold Temperature | 275-350° F. | 135-177° C. | |
| Drying | 4 hrs @ 300° F. | 4 hrs @ 149° C. | |
| Moisture Content | | | |
| Dew Point | 0.04% −20° F. | 0.04% −20° C. | |

In an alternative embodiment, mounting device 106 may comprise a rigid metal. The metal may comprise aluminum, anodized aluminum and stainless steel. For 6000 Series Aluminum Alloy; Aluminum Alloy; Metal; Nonferrous Metal, a property data table is provided as follows:

TABLE 4

| Component | Wt. % |
|---|---|
| Al | 95.8-98.6 |
| Cr | 0.04-0.35 |
| Cu | 0.15-0.4 |
| Fe | Max 0.7 |
| Mg | 0.8-1.2 |
| Mn | Max 0.15 |
| Other, each | Max 0.05 |
| Other total | Max 0.15 |
| Si | 0.4-0.8 |
| Ti | Max 0.15 |
| Zn | Max 0.25 |

TABLE 5

|  | Metric | English |
|---|---|---|
| Physical Properties | | |
| Density | 2.7 g/cc | 0.0975 lb/in³ |
| Mechanical Properties | | |
| Hardness Brinell | 95 | 95 |
| Hardness Knoop | 120 | 120 |
| Hardness Rockwell A | 40 | 40 |
| Hardness Rockwell B | 60 | 60 |
| Hardness Vickers | 107 | 107 |
| Ultimate Tensile Strength | 310 Mpa | 45000 psi |
| Tensile Yield Strength | 276 MPA | 40000 psi |
| Modulus of Elasticity | 68.9 GPa | 10000 ksi |
| Poisson's Ratio | 0.33 | 0.33 |
| Fatigue Strength | 96.5 Mpa | 14000 psi |
| Shear Modulus | 26 GPa | 3770 ksi |
| Shear Strength | 207 Mpa | 30000 psi |
| Electrical Properties | | |
| Electrical Resistivity | 3.99e−066 ohm-cm | 3.99e−066 ohm-cm |

The detail view of FIG. 3 illustrates an exploded view of exemplary mounting posts 102 attached to frame member 116. In some preferred embodiments, mounting post 102 includes a chamfered edge 300. Chamfered edge includes a dimensional measurement of approximately 0.15 inches±0.005 as measured from top 210 of mounting post 102 towards prescribed location 208. The chamfer may be cut at approximately a 45.00° angle. Mounting post 102 extends approximately 90.00" from a top surface of frame member 116. Chamfer cut 302 measures approximately Ø.10 inches±0.01 from an outside diameter of mounting post 102 towards the center (see also FIG. 5).

Turning to FIG. 4, centerline 200 runs generally down the middle of mounting device 106 and frame member 116 of trackable target probe 104. The asymmetry of cusps 108 of the astroid design is illustrated, for example, as shown about a z-plane running along center axis 400. An exemplary configuration of medical device 100 includes select dimensions to achieve proportions of medical device 100 components and a preferred asymmetric design of the present invention. For example, a length $d_3$ of mounting device 106 extending from attachment location 112 of trackable target probe 104 may be approximately 4.310 inches±0.005. The distance $d_4$ as measured from a first centerline 402 (corresponding to a first mounting post 102) measured to the end of mounting device 106 may be approximately 4.310 inches±0.005. The distance $d_5$ as measured from a second centerline 404 (corresponding to a second mounting post 102) measured to the end of mounting device 106 may be approximately 9.000 inches±0.005. The distance $d_6$ as measured from a third centerline 406 (corresponding to a third mounting post 102) measured to the end of mounting device 106 may be approximately 10.017 inches±0.005. The distance $d_7$ as measured from a fourth centerline 408 (corresponding to a fourth mounting post 102) measured to the end of mounting device 106 may be approximately 10.338 inches±0.005. The distance $d_8$ as measured from a fifth centerline 410 (corresponding to a fifth mounting post) 102 measured to the end of mounting device 106 may be approximately 11.950 inches±0.005. The height distance $h_1$ as measured from a vertical distance from the fifth centerline 410 (corresponding to a fifth mounting post 102) intersecting a perpendicular horizontal plane extending through the third centerline 406 (corresponding to a third mounting post 102) may be approximately 1.714 inches±0.005. The height distance $h_2$ as measured from a vertical distance from the fifth centerline 410 (corresponding to a fifth mounting post 102) intersecting a perpendicular horizontal plane extending through the fourth centerline 408 (corresponding to a fourth mounting post 102) may be approximately 1.734 inches±0.005. Thus $d_7>d_6$, and $h_2>h_1$.

FIG. 6 illustrates trackable target probe 104 having a marker element 600 mounted on mounting post 102. Marker element 600 may be designed as spherical marker element including a retro-reflective marker sphere, also referred to as passive reflective marker. Embodiments of retro-reflective marker spheres may include those used to aid registration and instrument tracking during image guided surgery procedures such as neurological procedures, spine procedures and orthopedic procedures. Embodiments may include a retro-reflective marker sphere having a high coefficient of retro-reflection on the external surface to provide feedback to the system/camera. Such surfaces may consist of micro glass spheres that reflect light. Depending on the medical application, different numbers and arrangements of retro-reflective marker spheres may be mounted on various types of surgical tools that may be used including that disclosed herein. Once mounted on a surgical probe, retro-reflective marker spheres provide an accuracy reference point for the surgical probe in three-dimensional space.

FIG. 7 is a detail view of the mounted marker element 600. Embodiments of marker element 600 may include internal structure 700 for receiving and mating with mounting post 102. In the disclosed embodiment, internal structure 700 is designed to not only mount marker element 600 to mounting post 102, but ensure that marker element 600 is consistently and accurately mounted such that a centerline 704 of marker element 600 is aligned with centerline 200 after mounting to frame member 116. For example, embodiments of the disclosed invention may provide an internal stop surface 702 that abuts the top 210 of mounting post 102. Upon doing so, centerline 704 of marker element 600 is aligned with centerline 200 of mounting device 106. Thus the rigidity of mounting device 106 is paramount to the design of the disclosed invention. Mounting device 106 does not flex in order to maintain this important attribute. Each mounting post 102 and marker element 600 of the disclosed invention is appropriately dimensioned such that in this manner, all mounted marker elements 600 mounted on trackable target probe 104 are automatically in alignment with centerline 200 when mounted in the disclosed manner.

Furthermore, embodiments of the disclosed invention provide that the materials and material characteristics described herein are well suited for medical device 100 to be utilized as a disposable single-use device being manufactured with marker elements 102 pre-attached to trackable probe 104 during the manufacturing process. A sterile single-use disposable marker device 100 of the disclosed invention may be packaged to maintain its sterile integrity and be ready for use upon request with the setup of the pre-attached marker elements 102 ready for use and correctly aligned along frame member 116. In operation, when a surgeon, for instance, opens the package containing the disclosed medical device 100, medical device 100 may be configured and employed within a surgical navigation system such as via mounting device 106. Upon assembly, the unique design of the disclosed embodiment automatically and consistently aligns marker elements 102 in alignment with suitable tolerance levels of the surgical navigation system requirements. The rigid mounting device 106 in combination with the gooseneck bend 114 design of the rigid frame marker 116 supports the correct and consistent alignment of marker elements 102 with respect to centerline 200 of mounting device 106. Disclosed embodiments provide centerline 200 automatically sync in correct alignment with the entire navigation system when mounted into a corresponding structure of the navigation system, such as via mounting device 106. This more easily facilitates setup efforts of the navigation system in a cost efficient manner and eliminates additional pre-registration and formatting procedures.

Having described the many embodiments of the present invention in detail, it will be apparent that modifications and variations are possible without departing from the scope of the present invention defined in the appended claims. For example, disclosed embodiments may provide certain indicia and/or colors on components of the disclosed disposable medical device such as, but not limited to, mounting device 106, frame member 116, flared extension portion 118, cusps 108, mounting posts 102 and/or marker elements 600. Such specific uses or applications associated with said indicia and/or colors may be employed, for example, in specific prescribed distinct surgical procedures or in certain environments or medical situations, or by specific groups of surgeons or individuals. These may include, but not limited to, for example, use in neuro and ENT surgery, spinal applications, soft/sensitive tissue applications and/or applying force applications. Additionally, other custom features may be employed and configured into the disclosed disposable medical device 100 such as pre-fashioned and custom made ergonomic grips/handles attachable to medical device 100, for example, via mounting device 100. An example of a coloring scheme is presented as follows:

TABLE 6

| Color of Component (e.g., handle/grip) | Probe Name | Tip Specific |
|---|---|---|
| Orange | Blunt Pointer | Pointer used for Neuro and ENT use; tip is slightly rounded (R 0.25 mm). |
| Blue | Sharp Pointer | Pointer used for spinal application; tip is harp, so that anatomical landmarks on bones can be acquired. |
| Green | Ball Pin Pointer | Pointer for touching soft, sensitive tissue; tip with ball (R 1.5 mm). |
| Yellow | Extra Strong Pointer | Pointer for applying force, pointer tip with big diameter (R 2.5 mm). |

Furthermore, it should be appreciated that pies in the present disclosure, while illustrating many embodiments of the present invention, are provided as non-limiting examples and are, therefore, not to be taken as limiting the various aspects so illustrated.

While the present invention has been disclosed with references to certain embodiments, numerous modifications, alterations, and changes to the described embodiments are possible without departing from the spirit and scope of the present invention, as defined in the appended claims. Accordingly, it is intended that the present invention not be limited to the described embodiments, but that it has the full scope defined by the language of the following claims, and equivalents thereof.

What is claimed is:

1. A device for a surgical navigation system, comprising:
a frame member having an attachment location;
a rigid mounting device disposed in the attachment location; and wherein the frame member comprises an upper portion connected to a lower portion via a bent portion,
wherein the lower portion comprises a plurality of mounting posts each having a top surface,
wherein a centerline extends through the rigid mounting device such that a horizontal plane running through the centerline aligns with each of the top surfaces,
wherein marker elements are mounted to the plurality of mounting posts such that upon mounting, a centerline of the marker elements aligns with the centerline extending through the rigid mounting device.

2. The device of claim 1, wherein the marker elements are spherical.

3. The device of claim 2, wherein the marker elements are light-reflecting spherical markers.

4. The device of claim 1, wherein the frame member is plastic.

5. The device of claim 4, wherein the plastic is selected from one of a polycarbonate, polyetheretherketone, and a polyetherimide material.

6. The device of claim 1, wherein the mounting device is metal.

7. The device of claim 6, wherein the metal is selected from one of aluminum, anodized aluminum, and stainless steel.

8. The device of claim 1, wherein the lower portion extends into a flared extension portion.

9. The device of claim 8, wherein the flared extension portion comprises an asymmetric configuration.

10. The device of claim 9, wherein the asymmetric configuration comprises an astroid design having four cusps.

11. The device of claim 10, wherein one of the plurality of mounting posts is disposed at endpoints of the astroid design.

12. The device of claim 11, wherein the astroid design comprises three endpoints having a respective one of the plurality of mounting posts attached thereto.

13. The device of claim 1, wherein the device comprises indicia disposed on the frame member.

14. A method of manufacturing a device comprising:
(a) configuring a frame member to form an upper portion and a lower portion connected by a bent portion;
(b) mounting a rigid mounting device to an attachment location of the upper portion, wherein a centerline extends through the rigid mounting device;
(c) connecting a plurality of mounting posts on the lower portion, wherein each plurality of mounting posts has a top surface, wherein the bent portion is configured such that a horizontal plane running through the centerline aligns with each top surface of the plurality of mounting posts; and
(d) mounting a marker element on each mounting post such that a centerline of each mounted marker element aligns with the top surface of the mounting post.

15. The method of claim 14, further comprising:
(e) extending the lower portion into a flared extension portion.

16. The method of claim 15, wherein the flared extension portion comprises an asymmetric configuration.

17. The method of claim 16, the asymmetric configuration comprises an astroid design having four cusps.

18. The method of claim 17, wherein one of the plurality of mounting posts is disposed at endpoints of the astroid design.

19. A method of manufacturing a medical device comprising:
(a) configuring a frame member to form an upper portion and a lower portion connected by a bent portion;
(b) mounting a rigid mounting device to an attachment location of the upper portion, wherein a centerline extends through the rigid mounting device; and
(c) mounting marker elements on the frame member, wherein the bent portion is configured such that a horizontal plane running through the centerline aligns with a centerline of each mounted marker element.

20. The method of claim 19, further comprising:
(d) extending the lower portion into a flared extension portion.

21. The method of claim 20, wherein the flared extension portion comprises an asymmetric configuration.

22. The method of claim 21, the asymmetric configuration comprises an astroid design having four cusps.

23. The method of claim 22, wherein the marker elements are mounted to a plurality of mounting posts disposed at endpoints of the astroid design.

24. A device for a surgical navigation system, comprising:
a frame member having an attachment location; and
a rigid mounting device disposed in the attachment location,
wherein a centerline extends through the rigid mounting device,
wherein the frame member comprises an upper portion connected to a lower portion via a bent portion,
wherein the lower portion comprises a plurality of mounting posts,
wherein marker elements are mounted to the plurality of mounting posts such that upon mounting, a centerline of the marker elements aligns with the centerline extending through the rigid mounting device.

25. The device of claim 24, wherein each of the plurality of mounting posts has a top surface, wherein a horizontal plane running through the centerline extending through the rigid mounting device aligns with each of the top surfaces.

26. The device of claim 24, wherein the lower portion extends into a flared extension portion.

27. The device of claim 26, wherein the flared extension portion comprises an asymmetric configuration.

28. The device of claim 27, wherein the asymmetric configuration comprises an astroid design having four cusps.

29. The device of claim 28, wherein one of the plurality of mounting posts is disposed at endpoints of the astroid design.

30. The device of claim 29, wherein the astroid design comprises three endpoints having a respective one of the plurality of mounting posts attached thereto.

* * * * *